US009421297B2

(12) United States Patent
Zhang et al.

(10) Patent No.: US 9,421,297 B2
(45) Date of Patent: Aug. 23, 2016

(54) STERILIZED COMPOSITIONS OF CYANOACRYLATE MONOMERS AND NAPHTHOQUINONE 2,3-OXIDES

(71) Applicant: Adhezion Biomedical, LLC, Wyomissing, PA (US)

(72) Inventors: Sheng Zhang, Hickory, NC (US); Rafael Ruiz, Sr., Hudson, NC (US); Shannon Phelps, Lenoir, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 0 days.

(21) Appl. No.: 14/243,203

(22) Filed: Apr. 2, 2014

(65) Prior Publication Data

US 2015/0283290 A1   Oct. 8, 2015

(51) Int. Cl.
| C08L 35/04 | (2006.01) |
| A61L 15/24 | (2006.01) |
| A61L 24/00 | (2006.01) |
| A61M 25/02 | (2006.01) |
| C09D 133/20 | (2006.01) |
| A61L 24/06 | (2006.01) |
| A61L 24/02 | (2006.01) |

(52) U.S. Cl.
CPC .......... *A61L 24/0015* (2013.01); *A61L 24/0021* (2013.01); *A61L 24/02* (2013.01); *A61L 24/06* (2013.01); *A61L 2300/428* (2013.01)

(58) Field of Classification Search
CPC ..... C08L 35/04; C08L 2203/02; A61L 15/24; A61L 26/0014; A61L 15/44; A61L 15/58; A61L 2300/404; A61L 26/0066; A61L 24/00; A61B 17/0057; A61B 17/10; A61M 25/02; A61M 25/04; C09D 133/20
See application file for complete search history.

(56) References Cited

U.S. PATENT DOCUMENTS

| 211,104 A | 1/1879 | Mulford |
| 334,046 A | 1/1886 | Pinkham |
| 1,221,227 A | 4/1917 | Shulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 2,794,788 A | 6/1957 | Coover, Jr. et al. |
| 2,912,454 A | 11/1959 | McKeever |
| 3,070,499 A | 12/1962 | Mullins et al. |
| 3,152,352 A | 10/1964 | Kosik, Jr. |
| 3,254,111 A | 5/1966 | Hawkins et al. |
| 3,260,637 A | 7/1966 | von Bramer |
| 3,282,773 A | 11/1966 | Wicker, Jr. et al. |
| 3,324,855 A | 6/1967 | Heimlich |
| 3,393,962 A | 7/1968 | Andrews |
| 3,451,538 A | 6/1969 | Trementozzi |
| 3,523,628 A | 8/1970 | Colvin et al. |
| 3,524,537 A | 8/1970 | Winter |
| 3,527,224 A | 9/1970 | Rabinowitz |
| 3,527,841 A | 9/1970 | Wicker, Jr. et al. |
| 3,540,577 A | 11/1970 | Trementozzi et al. |
| 3,564,078 A | 2/1971 | Wicker, Jr. et al. |
| 3,579,628 A | 5/1971 | Gander et al. |
| 3,607,542 A | 9/1971 | Leonard et al. |
| 3,614,245 A | 10/1971 | Schwartzman |
| 3,667,472 A | 6/1972 | Halpern |
| 3,692,752 A | 9/1972 | Setsuda et al. |
| 3,742,018 A | 6/1973 | O'Sullivan |
| 3,779,706 A | 12/1973 | Nablo |
| 3,797,706 A | 3/1974 | Mule |
| 3,836,377 A | 9/1974 | Delahunty |
| 3,863,014 A | 1/1975 | Mottus |
| 3,903,055 A | 9/1975 | Buck |
| 3,924,623 A | 12/1975 | Avery |
| 3,941,488 A | 3/1976 | Maxwell |
| 3,975,422 A | 8/1976 | Buck |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,038,345 A | 7/1977 | O'Sullivan et al. |
| 4,041,063 A | 8/1977 | Buck |
| 4,042,442 A | 8/1977 | Dombroski et al. |
| 4,057,535 A | 11/1977 | Lipatova et al. |
| 4,102,945 A | 7/1978 | Gleave |

(Continued)

FOREIGN PATENT DOCUMENTS

| DE | 2 261 261 | 7/1973 |
| DE | 40 09 621 | 10/1991 |

(Continued)

OTHER PUBLICATIONS

Beaton (Nutrition A Comprehensive Treatise 1964, Elsevier; pp. 63 and 64).*
The Merck Index 11th Ed. 1989, Merck 7 Co., Rahway, NJ: pp. 1580-1581; 2 pages.*
"Aclar®/Barex® Laminates: Flexible Solutions for Pharma Packaging" Drug Delivery Technology vol. 3, No. 3, May 2003, Posted on Mar. 28, 2008, http://www.drugdeliverytech.com/ME2/dirmod. asp?sid=&nm=&type=Publishing
&mod=Publications%3A%3AArticle
&mid=8F3A7027421841978F18BE895F87F791&tier=4
&Id=6EC6964EB29D46D8A297E499E57A4164.
Borrel et al. "The Effect of Crown Ethers, Tetraalkylammonioum Salts, and Polyoxyethylene Amphiphiles on Pirarubicin Incorporation in K562 Resistant Cells" Biochemical Pharmacology, vol. 50, No. 12., pp. 2069-2076, 1995.

(Continued)

*Primary Examiner* — Ernst V Arnold
(74) *Attorney, Agent, or Firm* — Stradley Ronon Stevens & Young, LLP

(57) ABSTRACT

Sterilized wound healing compositions comprise stabilized cyanoacrylate monomers homogenously mixed together with a naphthoquinone 2,3-oxide, including vitamin K oxides. The compositions are sterilized by irradiation, and the sterilized compositions are shelf stable such that their viscosity does not substantially increase following at least two years of shelf storage. The compositions may be used for closure of open wounds, and the compositions enhance the rate of wound healing relative to wounds not closed with the compositions.

16 Claims, No Drawings

(56) References Cited

U.S. PATENT DOCUMENTS

| | | |
|---|---|---|
| 4,105,715 A | 8/1978 | Gleave |
| 4,109,037 A | 8/1978 | Nohara |
| 4,142,630 A | 3/1979 | Hayes et al. |
| 4,170,585 A | 10/1979 | Motegi et al. |
| 4,171,416 A | 10/1979 | Motegi et al. |
| 4,182,823 A | 1/1980 | Schoenberg |
| 4,265,948 A | 5/1981 | Hayes et al. |
| 4,310,509 A | 1/1982 | Berglund et al. |
| 4,323,557 A | 4/1982 | Rosso et al. |
| 4,328,170 A | 5/1982 | Okawara et al. |
| 4,340,043 A | 7/1982 | Seymour |
| 4,364,876 A | 12/1982 | Kimura et al. |
| 4,374,126 A | 2/1983 | Cardarelli et al. |
| 4,377,490 A | 3/1983 | Shiraishi et al. |
| 4,386,193 A | 5/1983 | Reich et al. |
| 4,413,753 A | 11/1983 | Stock |
| 4,439,196 A | 3/1984 | Higuchi |
| 4,444,933 A | 4/1984 | Columbus et al. |
| 4,447,224 A | 5/1984 | DeCant, Jr. et al. |
| 4,447,233 A | 5/1984 | Mayfield |
| 4,460,759 A | 7/1984 | Robins |
| 4,475,916 A | 10/1984 | Himmelstein |
| 4,480,940 A | 11/1984 | Woodruff |
| 4,486,194 A | 12/1984 | Ferrara |
| 4,487,603 A | 12/1984 | Harris |
| 4,533,422 A | 8/1985 | Litke |
| 4,542,012 A | 9/1985 | Dell |
| 4,551,366 A | 11/1985 | Maruhashi et al. |
| 4,554,686 A | 11/1985 | Baker |
| 4,643,181 A | 2/1987 | Brown |
| 4,646,765 A | 3/1987 | Cooper et al. |
| 4,649,909 A | 3/1987 | Thompson |
| 4,652,763 A | 3/1987 | Nablo |
| 4,685,591 A | 8/1987 | Schaefer et al. |
| 4,713,235 A | 12/1987 | Krall |
| 4,718,966 A | 1/1988 | Harris et al. |
| 4,772,148 A | 9/1988 | Buschemeyer |
| 4,786,534 A | 11/1988 | Aiken |
| 4,818,325 A | 4/1989 | Hiraiwa et al. |
| 4,925,678 A | 5/1990 | Ranney |
| 4,959,217 A | 9/1990 | Sanders et al. |
| 4,977,892 A | 12/1990 | Ewall |
| 4,978,527 A | 12/1990 | Brink et al. |
| 4,994,542 A | 2/1991 | Matsuda et al. |
| 5,009,654 A | 4/1991 | Minshall et al. |
| 5,039,753 A | 8/1991 | Woods et al. |
| 5,042,690 A | 8/1991 | O'Meara |
| 5,051,256 A | 9/1991 | Barnes |
| 5,069,907 A | 12/1991 | Mixon et al. |
| 5,083,685 A | 1/1992 | Amemiya et al. |
| 5,131,777 A | 7/1992 | Kimura et al. |
| 5,135,964 A | 8/1992 | Lee et al. |
| 5,167,616 A | 12/1992 | Haak et al. |
| 5,169,383 A | 12/1992 | Gyory et al. |
| 5,192,536 A | 3/1993 | Huprich |
| 5,225,182 A | 7/1993 | Sharma |
| 5,232,774 A | 8/1993 | Otsuka et al. |
| 5,236,703 A | 8/1993 | Usala |
| 5,240,525 A | 8/1993 | Percec et al. |
| 5,254,132 A | 10/1993 | Barley et al. |
| 5,283,034 A | 2/1994 | Okrongly et al. |
| 5,288,159 A | 2/1994 | Wirt |
| 5,302,629 A | 4/1994 | Berejka |
| 5,306,490 A | 4/1994 | Barley, Jr. |
| 5,312,864 A | 5/1994 | Wenz et al. |
| 5,328,687 A | 7/1994 | Leung et al. |
| 5,344,670 A | 9/1994 | Palmer et al. |
| 5,350,798 A | 9/1994 | Linden et al. |
| 5,358,349 A | 10/1994 | Burroughs et al. |
| 5,370,221 A | 12/1994 | Magnusson et al. |
| 5,403,591 A | 4/1995 | Tighe et al. |
| 5,411,345 A | 5/1995 | Ueji et al. |
| 5,453,457 A | 9/1995 | Meltzer et al. |
| 5,457,141 A | 10/1995 | Matsuda et al. |
| 5,470,597 A | 11/1995 | Mendenhall |
| 5,475,110 A | 12/1995 | Hudkins et al. |
| 5,480,935 A | 1/1996 | Greff et al. |
| 5,510,391 A | 4/1996 | Elson |
| 5,530,037 A | 6/1996 | McDonnell et al. |
| 5,547,662 A | 8/1996 | Khan et al. |
| 5,561,198 A | 10/1996 | Huver et al. |
| 5,665,817 A | 9/1997 | Greff et al. |
| 5,684,042 A | 11/1997 | Greff et al. |
| 5,730,994 A | 3/1998 | Askill et al. |
| 5,749,956 A | 5/1998 | Fisher et al. |
| 5,762,919 A | 6/1998 | Greff et al. |
| 5,783,177 A | 7/1998 | Greff et al. |
| 5,803,086 A | 9/1998 | Scholz et al. |
| 5,807,563 A | 9/1998 | Askill et al. |
| 5,811,091 A | 9/1998 | Greff et al. |
| 5,866,106 A | 2/1999 | Papay |
| 5,874,044 A | 2/1999 | Kotzev |
| 5,902,594 A | 5/1999 | Greff et al. |
| 5,916,882 A | 6/1999 | Jeng |
| 5,928,611 A | 7/1999 | Leung |
| 5,944,754 A | 8/1999 | Vacanti |
| 5,957,877 A | 9/1999 | Askill et al. |
| 5,979,450 A | 11/1999 | Baker et al. |
| 5,981,621 A | 11/1999 | Clark et al. |
| 5,985,395 A | 11/1999 | Comstock et al. |
| 5,998,472 A | 12/1999 | Berger et al. |
| 6,086,906 A | 7/2000 | Greff et al. |
| 6,090,397 A | 7/2000 | Lee et al. |
| 6,099,807 A | 8/2000 | Leung |
| 6,136,326 A | 10/2000 | Kotzev |
| 6,143,352 A | 11/2000 | Clark et al. |
| 6,143,805 A | 11/2000 | Hickey et al. |
| 6,155,265 A | 12/2000 | Hammerslag |
| 6,217,603 B1 | 4/2001 | Clark et al. |
| 6,228,354 B1 | 5/2001 | Jeng |
| 6,245,933 B1 | 6/2001 | Malofsky et al. |
| 6,248,800 B1 | 6/2001 | Greff et al. |
| 6,294,629 B1 | 9/2001 | O'Dwyer et al. |
| 6,299,631 B1 | 10/2001 | Shalaby |
| 6,310,166 B1 | 10/2001 | Hickey et al. |
| 6,323,275 B2 | 11/2001 | Takahashi et al. |
| 6,342,213 B1 | 1/2002 | Barley et al. |
| 6,352,704 B1 | 3/2002 | Nicholson et al. |
| 6,488,665 B1 | 12/2002 | Severin et al. |
| 6,492,434 B1 | 12/2002 | Barley, Jr. et al. |
| 6,495,229 B1 | 12/2002 | Carte et al. |
| 6,547,917 B1 | 4/2003 | Misiak et al. |
| 6,579,469 B1 | 6/2003 | Nicholson et al. |
| 6,605,667 B1 | 8/2003 | Badejo et al. |
| 6,620,846 B1 | 9/2003 | Jonn et al. |
| 6,626,296 B1 | 9/2003 | Jimu et al. |
| 6,667,031 B2 | 12/2003 | Azevedo |
| 6,699,940 B2 | 3/2004 | Shalaby |
| 6,742,522 B1 | 6/2004 | Baker et al. |
| 6,743,858 B2 | 6/2004 | Hickey et al. |
| 6,746,667 B2 | 6/2004 | Badejo et al. |
| 6,767,552 B2 | 7/2004 | Narang |
| 6,779,657 B2 | 8/2004 | Mainwaring et al. |
| 6,797,107 B1 | 9/2004 | Kotzey |
| 6,802,416 B1 | 10/2004 | D'Alessio et al. |
| 6,849,082 B2 | 2/2005 | Azevedo |
| 6,881,421 B1 | 4/2005 | daSilveira et al. |
| 6,896,838 B2 | 5/2005 | D'Alessio |
| 6,942,875 B2 | 9/2005 | Hedgpeth |
| 6,960,040 B2 | 11/2005 | D'Alessio et al. |
| 6,974,585 B2 | 12/2005 | Askill |
| 6,977,278 B1 | 12/2005 | Misiak |
| 6,995,227 B2 | 2/2006 | Ryan et al. |
| 7,255,874 B1 | 8/2007 | Bobo et al. |
| 7,939,568 B2 | 5/2011 | Marchal |
| 8,211,947 B2 | 7/2012 | Selman-Housein Sosa |
| 8,283,382 B2 | 10/2012 | Perez-Soler et al. |
| 8,293,838 B2 | 10/2012 | Zhang et al. |
| 2002/0002223 A1 | 1/2002 | Cox et al. |
| 2002/0037272 A1 | 3/2002 | Askill et al. |
| 2003/0044380 A1 | 3/2003 | Zhu et al. |
| 2003/0077386 A1 | 4/2003 | Azevedo |
| 2003/0135016 A1 | 7/2003 | Tajima et al. |
| 2003/0149128 A1 | 8/2003 | Malofsky et al. |

(56) References Cited

U.S. PATENT DOCUMENTS

| | | |
|---|---|---|
| 2003/0158579 A1 | 8/2003 | Azevedo |
| 2003/0158580 A1 | 8/2003 | Azevedo |
| 2004/0115274 A1 | 6/2004 | Cox et al. |
| 2004/0120849 A1 | 6/2004 | Stewart et al. |
| 2004/0126355 A1 | 7/2004 | Childers |
| 2004/0127738 A1 | 7/2004 | Azevedo |
| 2004/0253039 A1 | 12/2004 | Stenton |
| 2005/0042266 A1 | 2/2005 | Narang |
| 2005/0047846 A1 | 3/2005 | Narang et al. |
| 2005/0067312 A1 | 3/2005 | Gupta et al. |
| 2005/0142163 A1 | 6/2005 | Hunter et al. |
| 2005/0147582 A1 | 7/2005 | Zimmerman et al. |
| 2005/0182347 A1 | 8/2005 | Bishop et al. |
| 2005/0196431 A1 | 9/2005 | Narang et al. |
| 2005/0197421 A1 | 9/2005 | Loomis |
| 2005/0281866 A1 | 12/2005 | Jarrett et al. |
| 2005/0284487 A1 | 12/2005 | Gellerstedt et al. |
| 2006/0062687 A1 | 3/2006 | Morales |
| 2006/0275229 A1 | 12/2006 | Pillai et al. |
| 2007/0025950 A1 | 2/2007 | Elson |
| 2007/0041935 A1 | 2/2007 | Salamone et al. |
| 2007/0048356 A1 | 3/2007 | Schorr et al. |
| 2007/0078207 A1 | 4/2007 | Jonn et al. |
| 2007/0092481 A1 | 4/2007 | Misiak et al. |
| 2007/0092483 A1 | 4/2007 | Pollock |
| 2007/0147947 A1 | 6/2007 | Stenton et al. |
| 2007/0244490 A1 | 10/2007 | Moehle et al. |
| 2008/0021139 A1 | 1/2008 | Blacklock et al. |
| 2008/0078413 A1 | 4/2008 | Padget et al. |
| 2008/0102053 A1 | 5/2008 | Childers |
| 2008/0220094 A1 | 9/2008 | Bobyock et al. |
| 2008/0319063 A1 | 12/2008 | Zhang |
| 2009/0234022 A1 | 9/2009 | Salentine et al. |
| 2009/0317353 A1 | 12/2009 | Zhang et al. |
| 2010/0035997 A1 | 2/2010 | Broadley et al. |
| 2010/0112036 A1 | 5/2010 | Zhang et al. |
| 2010/0130618 A1 | 5/2010 | Vaidya et al. |
| 2010/0269749 A1 | 10/2010 | Badejo et al. |
| 2010/0324148 A1 | 12/2010 | Perez-Soler et al. |
| 2012/0184609 A1 | 7/2012 | Jamison et al. |

FOREIGN PATENT DOCUMENTS

| | | |
|---|---|---|
| DE | 2010 3336 | 5/2001 |
| DE | 10 2007 019 044 | 10/2008 |
| EP | 0127466 | 12/1984 |
| EP | 0271675 | 6/1988 |
| FR | 2700698 | 7/1994 |
| GB | 1230560 | 5/1971 |
| GB | 2200124 | 7/1988 |
| JP | 59-066471 | 4/1984 |
| JP | 62-022877 | 1/1987 |
| JP | 03-207778 | 9/1991 |
| JP | H05320039 | 12/1993 |
| JP | 10-140091 | 5/1998 |
| WO | WO96/14292 | 5/1996 |
| WO | WO96/23532 | 8/1996 |
| WO | WO99/10020 | 3/1999 |
| WO | WO03/70257 | 8/2003 |
| WO | WO2004/045498 | 6/2004 |
| WO | WO2006/073922 | 7/2006 |
| WO | WO2009/003017 | 12/2008 |
| WO | WO2009/064291 | 5/2009 |

OTHER PUBLICATIONS

Cameron, J.L. et al., "The Degradation of Cyanoacrylate Tissue Adhesive, pt. 1", Surgery, vol. 58, Iss. 2, Aug. 1965, pp. 424-430.
Canale, A.J., et al., "Methyl a-cyanoacrylate. I. Free-radical homopolymerization", Journal of Applied Polymer Science, vol. 4, No. 11, Sep./Oct. 1960, pp. 231-236 [Abstract Only].
Collins et al., "Biological Substrates and Cure Rates of Cyanoacrylate Tissue Adhesives" Archives of Surgery vol. 93, Sep. 1966, 428-432.
Darwish et al., "The evaluation of crown ether based niosomes as cation containing and cation sensitive drug delivery systems" International Journal of Pharmaceutics 159 (1997) 207-213.
Dumont et al., "New Oligosaccharidic Crown Ethers as Potential Drug-Targetting Vectors: Synthesis & Biological Evaluation" Bioorganic & Medicinal Chemistry Letters, vol. 4, No. 9, pp. 1123-1126, 1994.
Fussnegger, B. "Poloxamers (1) Lutrol® F 68 (Poloxamer 188)." BASF ExAct, Nov. 1999, 5-6.
Garnier-Suillerot et al., "Analysis of Drug Transport Kinetics in Multidrug-resistant Cells: Implications for Drug Action" Current Medicinal Chemistry, 2001, 8, 51-64.
Gurnaney, H., et al., "Dermabond Decreases Pericatheter Local Anesthetic Leakage After Continuous Perineural Infusions," Anesthesia & Analgesia, 2011, p. 206.
Hansen, "Fast Cure—High moisture vapor transmission rate adhesives improve wound care." Adhesives Age Mar. 2003, 22, 24-25.
International Search Report and Written Opinion dated Dec. 8, 2010 for international application No. PCT/US2009/062761.
Lehman et al., "Toxicity of Alkyl 2-Cyanoacrylates", Archives of Surgery, vol. 93, Issue 3, Sep. 1966, pp. 441-446.
Leonard, F, "Hemostatic Applications of Alpha Cyanoacrylates: Bonding Mechanism and Physiological Degradation of Bonds", Adhesion in Biological Systems, ed. R.S. Manly, 1970, pp. 185-199.
Leonard, F. et al., "Interfacial Polymerization of n-Alkyl a-Cyanoacrylate Homologs", Journal of Applied Polymer Science, vol. 10 1966, pp. 1617-1623.
Leonard, F. et al., "Synthesis and Degradation of Poly (alkyl a-Cyanoacrylates)", Journal of Applied Polymer Science, vol. 10, Iss 8, Aug. 1966, p. 1214.
Leonard, F. et al., "Synthesis and Degradation of Poly(alkyl a-Cyanoacrylates)", Journal of Applied Polymer Science, vol. 10, Iss. 2, Feb. 1966, pp. 259-272.
Material Safety Data Sheet (MSDS) of 2-octyl cyanoacrylate; Jun. 2, 2004.
Material Safety Data Sheet (MSDS) of isobuthyl-2-cyanoacrylate; Sep. 25, 1998.
Material Safety Data Sheet (MSDS) of n-butyl cyanoacrylate; Oct. 19, 2009 and Jun. 2, 2004.
Quinn, J.V., "Clinical Approaches to the Use of Cyanoacrylate Tissue Adhesives", Tissue Adhesives in Clinical Medicine, Second Edition, 2005, BC Decker, Inc., pp. 27-76.
Simonova, G., et al., "Cyanoacrylate tissue adhesives-effective securement technique for intravascular catheters: in vitro testing safety and feasibility," Anaesthesia and Intensive Care, vol. 40, No. 3, May 2012, pp. 460-466.
Tseng, Y.C. et al., "Modification of synthesis and investigation of properties for 2-cyanoacrylates", Biomaterials, vol. 11, Jan. 1990, pp. 73-79.
Uchegbu et al., "Non-ionic surfactant based vesicles (niosomes) in drug delivery" International Journal of Pharmaceutics 172 (1998) 33-70.
Vezin, W.R. et al., "Diffusion of Small Molecules in Poly-n-Alkyl Cyanoacrylates", British Pharmaceutical Conference 1978—Communications presented at the 115th meeting, Coventry, Sep. 11-15, 1978, Journal of Pharmacy and Pharmacology, vol. 30, Issue: Suppl, Dec. 1978, p. 2P.
Vezin, W.R. et al., "In vitro heterogeneous degradation of poly(n-alkyl a-cyanoacrylates)", Journal of Biomedical Materials Research, vol. 14, 1980, pp. 93-106.
Wilkinson, J.N., et al., "Securing epidural catheters with Histocryl glue," Anaesthesia, 2008, 63, pp. 316-327.
Wilkinson, J.N., et al., "Tissue adhesive as an alternative to sutures for securing central venous catheters", Anaesthesia, 2007, 62, pp. 966-974.
Woodward, S.C. et al., "Histotoxicity of Cyanoacrylate Tissue Adhesives in the Rat", Annals of Surgery, vol. 162, No. 1, Jul. 1965, pp. 113-122.
Yonezawa, M. et al., "Studies on a-Cyanoacrylate, VI: Reaction of Cyanoacetate with Formaldehyde" Yuki Gosei Kagaku Kyokaishi, vol. 25, Iss 4, Apr. 1967, pp. 311-316.

* cited by examiner

STERILIZED COMPOSITIONS OF CYANOACRYLATE MONOMERS AND NAPHTHOQUINONE 2,3-OXIDES

FIELD OF THE INVENTION

The invention relates generally to the field of cyanoacrylate monomer chemistry, and more particularly to compositions of cyanoacrylate monomers homogenously mixed together with vitamin K oxide and sterilized. The compositions may be used, for example, to close open wounds and facilitate healing.

BACKGROUND OF THE INVENTION

Various publications, including patents, published applications, technical articles and scholarly articles are cited throughout the specification. Each of these cited publications is incorporated by reference herein, in its entirety and for all purposes.

Traditional wound healing methods includes using topical liquid or semi-solid formulations. Such topical formulations typically only maintain contact with the wound for a short period of time, or may be rapidly absorbed, in either case limiting the efficiency of the formulation toward facilitating wound healing. Although dressings such as gauze, cotton, wool, and bandages can maintain the formulation in the vicinity of the wound for longer, the inability to maintain moisture may impede the effects of the dressings.

For more serious wounds, tissue adhesives, hydrocolloids, hydrogels, polymer films, biological dressings, foam dressings, and alginate may be used as a wound dressing. In addition, cyanoacrylate-based tissue adhesives may be used. Cyanoacrylate adhesives offer advantages over sutures or staples insofar as they produce lower infection rates.

It is believed that some cyanoacrylate compositions may have antimicrobial properties, although this has not translated into enhancing wound healing. Accordingly, some cyanoacrylate adhesive compositions for medical uses have wound healing accelerating agents incorporated therein. For example, U.S. Pat. Nos. 5,684,042, 5,762,919, 5,811,091, and 5,783,177 and U.S. Publication No. 20050042266 describe the inclusion of antimicrobial agents in a cyanoacrylate adhesive composition, for purposes of promoting wound healing.

Nevertheless, it is difficult to incorporate different additives into cyanoacrylate adhesives. First, most additives are not soluble in or miscible with cyanoacrylates. Second, of those additives that may dissolve, most affect the polymerization of the monomers—either by inhibiting it (renders the adhesive useless) or causing it (prevents shelf storage or disposition from a container). Thus, the cyanoacrylate could be prevented from curing (polymerizing) or induced to prematurely polymerize resulting in an undesirable reduction or destruction of the shelf-life stability of the cyanoacrylate. Third, some additives affect the viscosity of the composition. Fourth, some additive affect the performance of the composition in terms of elongating the cure time and diminishing the bonding strength. Fifth, some additives interact with the cyanoacrylate monomers, which in turn inactivates the additives or diminishes their efficacy as explained in U.S. Pat. No. 5,684,042. Sixth, cyanoacrylate adhesives are difficult to sterilize because all known sterilization modalities induce polymerization of the monomers, and additives tend to further facilitate this sterilization-induced polymerization. Thus, cyanoacrylate adhesives present many challenges of compatibility for potential wound healing accelerating agents.

Therefore a need remains for imparting wound-healing properties into cyanoacrylate adhesive compositions used for medical purposes via wound-healing additives that do not harm the integrity of the cyanoacrylate monomers or the additives themselves. A further need remains for the ability to sterilize wound-healing agent-containing cyanoacrylate adhesive compositions without affecting the shelf stability of the composition.

SUMMARY OF THE INVENTION

The invention features sterilized cyanoacrylate adhesive compositions. The compositions may comprise at least about 85% by weight of a cyanoacrylate monomer, from about 5,000 ppm to about 16,000 ppm of butylated hydroxyl anisole, from about 20 ppm to about 150 ppm of sulfur dioxide, about from 0.1% to about 15% by weight of a naphthoquinone 2,3-oxide, including any homolog or derivative thereof, or of a vitamin K2 oxide. The compositions may further comprise from about 10 ppm to about 6000 ppm of a polymerization accelerator. In the compositions, the naphthoquinone 2,3-oxide or vitamin K2 oxide is miscible with and homogenously mixed together with the cyanoacrylate monomer. The homogenous mixture is sterilized by ethylene oxide, irradiation, or both ethylene oxide and irradiation. Following sterilization, the viscosity of the sterilized composition is no more than about 200 centipoise after at least two years of shelf storage at ambient conditions. The two years may be measured according to an advanced aging analysis, for example, by storage at 80 degrees C. for at least 13 days.

The cyanoacrylate monomer preferably comprises 2-octyl cyanoacrylate, n-butyl cyanoacrylate, or a mixture of 2-octyl cyanoacrylate and n-butyl cyanoacrylate. The cyanoacrylate monomer may comprise 2-octyl cyanoacrylate, n-octyl cyanoacrylate, 2-ethyl hexyl cyanoacrylate, pentyl-cyanoacrylate, 1-methyl-butyl-cyanoacrylate, neopentyl-cyanoacrylate, hexyl-cyanoacrylate, 1-methyl pentyl-cyanoacrylate, heptyl-cyanoacrylate, nonyl-cyanoacrylate, decyl-cyanoacrylate, undecyl-cyanoacrylate, dodecyl-cyanoacrylate, isopropoxyethyl-cyanoacrylate, butyl cyanoacrylate, or any isomer and/or mixtures thereof.

The composition may comprise from about 0.05% to about 12% by weight of the naphthoquinone 2,3-oxide or from about 0.05% to about 12% by weight of vitamin K2. The naphthoquinone 2,3-oxide preferably comprises a vitamin K oxide. The vitamin K oxide may comprise vitamin K1 oxide, vitamin K2 oxide, vitamin K3 oxide, vitamin K4 oxide, vitamin K5 oxide, vitamin K6 oxide, vitamin K7 oxide, or any combination thereof. Vitamin K1 oxide is highly preferred.

In some aspects, the naphthoquinone 2,3-oxide or derivative thereof comprises an oxide of any of the following: vitamin K1 (2-methyl-3-phytyl-1,4-naphthoquinone), menadione (vitamin K3; 2-methyl-1,4-naphthoquinone), vitamin K4 (1,4-diacetoxy-2-methylnaphthalene), vitamin K5 (4-amino-2-methyl-1-naphthalenol), vitamin K6, vitamin K7 (3-methyl-4-amino-1-naphthol hydrochloride), dihydrovitamin K, menaquinone-4, menaquinone-6, menaquinone-7, menadiol, menadiol sodium diphosphate, menadiol diacetate, menadoxime, or any combination thereof. In some aspects, a menaquinone comprises an oxide of vitamin K2 (2-methyl-3-hexaprenyl-1,4-naphthoquinone), also known in the art as menaquinone oxide or menadione epoxide.

When the polymerization accelerator is included, the composition comprises from about 10 ppm to about 6000 ppm of the polymerization accelerator. The polymerization accelerator preferably comprises a crown ether. The crown ether polymerization accelerator preferably comprises 18-crown-6 crown ether.

The composition may optionally comprise a plasticizing agent. The composition may optionally comprise a thickening agent. The composition may optionally comprise a dye. The composition may optionally comprise a plasticizing agent and a thickening agent. The composition may optionally comprise a plasticizing agent, a thickening agent, and a dye. These additional agents may be included in a composition that comprises a polymerization accelerator.

The irradiation used to sterilize the composition may comprise electron-beam, gamma, x-ray, or microwave irradiation. Gamma sterilization is preferred in some aspects. Electron beam (E-beam) sterilization is preferred in some aspects. Irradiation may be used in combination with chemical sterilization, such as ethylene oxide sterilization in some aspects.

The compositions may be packaged in a kit. The kit may comprise the composition and a container, which container may comprise an applicator. The kit also may comprise instructions for using the composition, for example, instructions for using the composition in a method for closing a wound, or instructions for using the composition in a method for securing a catheter. Such methods may be any method described or exemplified herein. The container of the kit may comprise an acrylonitrile copolymer. The container may comprise multiple layers, with the inner layer comprising an acrylonitrile copolymer. Preferably, the composition is contained in the container.

A method for closing an open wound on a subject in need thereof comprises applying a composition such as those above or any composition described or exemplified herein to the wound and allowing the composition to cure over the wound, thereby closing the wound. The open wound may comprise trauma. The open wound may comprise a skin ulcer, including a pressure ulcer such as bed sores. A method for securing a catheter inserted into a subject comprises applying a composition such as those above or any composition described or exemplified herein to a surface on the body, to a surface on the catheter, or to a surface on the body and a surface on the catheter and allowing the composition to cure between the surface of the body and the surface of the catheter, thereby securing the catheter in place. The catheter may comprise, for example, an intravenous catheter, an epidural catheter, a shunt, or any other catheter inserted into the skin. The composition may cure over the catheter insertion point, thereby sealing the insertion wound.

DETAILED DESCRIPTION OF THE INVENTION

Various terms relating to aspects of the present invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The terms "subject" or "patient" are used interchangeably. A subject may be any animal, including mammals such as companion animals, laboratory animals, and non-human primates. Human beings are preferred.

It has been observed in accordance with the invention that vitamin K oxides, and derivatives thereof are miscible with cyanoacrylate monomers, and that mixtures of cyanoacrylate monomers and vitamin K oxides or derivatives thereof can be sterilized without inducing premature polymerization of the monomers. Moreover, the sterilized mixtures can be stored for at least two years without substantial increases in viscosity and without premature curing. Accordingly, the invention features sterilized compositions of cyanoacrylate monomers mixed together with vitamin K oxides, or derivatives thereof. The vitamin K oxides, and derivatives thereof, remain miscible in the cyanoacrylate monomers following sterilization, and during shelf storage for at least two years. The compositions may be used, for example, for closure of open wounds.

The compositions include cyanoacrylate monomers, which are in liquid form. Monomers that may be used in this invention are readily polymerizable, e.g., anionically polymerizable or free radical polymerizable, to form polymers. Preferred monomers include 1,1-disubstituted ethylene monomers of the formula (I):

wherein X and Y are each strong electron withdrawing groups, and R is H, —CH=CH2, or provided that X or Y is a cyano group, R is a C1-C4 alkyl group.

Examples of monomers within the scope of formula (I) include alpha-cyanoacrylates, vinylidene cyanides, C1-C4 alkyl homologues of vinylidene cyanides, dialkyl methylene malonates, acylacrylonitriles, vinyl sulfinates and vinyl sulfonates of the formula CH2=CX'Y wherein X' is —SO2R' or —SO3R' and Y' is —CN, —COOR', —COCH3, —SO2R' or —SO3R', and R' is H or hydrocarbyl.

Preferred monomers of formula (I) include alpha-cyanoacrylates having formula (II):

wherein R2 is hydrogen and R3 is a hydrocarbyl or substituted hydrocarbyl group; a group having the formula —R4-O—R5-O—R6, wherein R4 is a 1,2-alkylene group having 2-4 carbon atoms, R5 is an alkylene group having 2-12 carbon atoms, and R6 is an alkyl group having 1-6 carbon atoms; or a group having the formula:

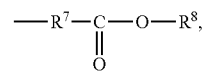

wherein R7 is:

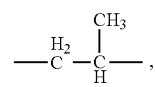

or —[C(CH₃)₂]ₙ—
wherein n is 1-10, preferably 1-8 carbon atoms and R8 is an organic moiety.

Examples of suitable hydrocarbyl and substituted hydrocarbyl groups include straight chain or branched chain alkyl groups having 1-16 carbon atoms; straight chain or branched chain C1-C16 alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; arylalkyl groups; alkylaryl groups; and aryl groups.

The moiety R8 may be substituted or unsubstituted, and may be straight chain, branched or cyclic, saturated, unsaturated or aromatic. Examples of such organic moieties include C1-C8 alkyl moieties, C2-C8 alkenyl moieties, C2-C8 alkynyl moieties, C3-C12 cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro- and bromosubstituted hydrocarbons) and oxy-(e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 8 carbon atoms.

In the cyanoacrylate monomer of formula (II), R3 is preferably an alkyl group having 1-10 carbon atoms or a group having the formula -AOR9, wherein A is a divalent straight or branched chain alkylene or oxyalkylene moiety having 2-8 carbon atoms, and R9 is a straight or branched alkyl moiety having 1-8 carbon atoms. Examples of groups represented by the formula -AOR9 include 1-methoxy-2-propyl, 2-butoxy ethyl, isopropoxy ethyl, 2-methoxy ethyl, and 2-ethoxy ethyl.

Non-limiting examples of suitable cyanoacrylate monomers include methyl cyanoacrylate, ethyl cyanoacrylate, n-propyl cyanoacrylate, isopropyl cyanoacrylate, n-butyl cyanoacrylate, isobutyl cyanoacrylate, 3-acetoxypropyl cyanoacrylate, 2-methoxypropyl cyanoacrylate, and 3-chloropropyl cyanoacrylate, n-pentyl cyanoacrylate, iso-pentyl cyanoacrylate, n-hexyl cyanoacrylate, iso-hexyl cyanoacrylate, n-heptyl cyanoacrylate, 2-ethylhexyl cyanoacrylate, n-octyl cyanoacrylate, 2-octyl cyanoacrylate, nonyl cyanoacrylate, decyl cyanoacrylate. Combinations of these monomers may be employed. Highly preferred monomers include 2-octyl cyanoacrylate and n-butyl cyanoacrylate, which may be used individually or in combination.

The cyanoacrylate monomer may comprise about 90% to about 99% by weight of the composition. The cyanoacrylate monomer may comprise about 90% to about 98% by weight of the composition. The cyanoacrylate monomer may comprise about 90% to about 97% by weight of the composition. The cyanoacrylate monomer may comprise about 95% to about 99% by weight of the composition. The cyanoacrylate monomer may comprise about 95% to about 98% by weight of the composition. The cyanoacrylate monomer may comprise about 95% to about 97% by weight of the composition. The cyanoacrylate monomer may comprise about 94% to about 99% by weight of the composition. The cyanoacrylate monomer may comprise about 94% to about 98% by weight of the composition. The cyanoacrylate monomer may comprise about 94% to about 97% by weight of the composition. The cyanoacrylate monomer may comprise about 97% to about 99% by weight of the composition. The cyanoacrylate monomer may comprise about 97% to about 98% by weight of the composition. The cyanoacrylate monomer may comprise about 90%, about 91%, about 92%, about 93%, about 94%, about 95%, about 96%, about 97%, about 98%, about 99%, or more than 99% by weight of the composition.

The cyanoacrylate monomer may comprise a high level of purity. The purity of cyanoacrylate may be at least about 97% by weight, preferably at least about 98% by weight, and more preferably at least about 99% by weight of the cyanoacrylate monomer. The purity of cyanoacrylate monomer may be determined during and/or after a distillation process. High purity may be obtained, for example, by multiple distillations under high vacuum and high temperature. The vacuum for distilling cyanoacrylate monomer is in the range of about 0.02 Torr to about 15 Torr, preferably in the range of about 0.05 Torr to about 10 Torr, and more preferably in the range of about 0.1 Torr to about 10 Torr. The distillation temperature is in the range of about 100° C. to about 180° C., preferably in the range of about 100° C. to about 160° C., and more preferably in the range of about 100° C. to about 150° C.

The distilled cyanoacrylate monomers may be filtered through one or multiple filters in order to reduce the bioburden level of the cyanoacrylate composition and remove any immiscible impurities or contaminants. If filtered, the cyanoacrylate monomers may be filtered through any suitable sized filters known in the art. For example, in a multiple step filtration process, the cyanoacrylate monomers may be filtered through a primary filter and one or more additional or secondary filters. The size of the primary filter may range, for example, on the order of about 0.01 to about 0.8 μm, preferably in the range of about 0.01 to about 0.6 μm, and more preferably in the range of about 0.03 to about 0.6 μm. The size of the additional or secondary filters may range, for example, on the order of about 1 to about 200 μm, preferably in the range of about 1 to about 150 μm, and more preferably in the range of about 1 to about 100 μm.

Preferably, the cyanoacrylate monomers are stabilized, such that the compositions comprise one or more stabilizers. The stabilizers may include either or both of free radical stabilizers and anionic stabilizers. Thus, for example, the composition may comprise one or more free radical stabilizers, one or more anionic stabilizers, or one or more of each of free radical stabilizers and anionic stabilizers.

Free radical stabilizers that may be used include without limitation, hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4methoxyphenol; 2,2-methylene-bis-(4-methyl-6-tert-butylphenol). In preferred aspects, the free radical stabilizer is butylated hydroxyl anisole (BHA).

The free radical stabilizer may be used in an amount effective to stabilize the cyanoacrylate monomers such that the monomers do not substantially polymerize prematurely, either before or after sterilization and any subsequent shelf storage. A free radical stabilizer such as BHA may comprise about from 200 ppm to about 16,000 ppm of the composition. The free radical stabilizer may comprise from about 5000 ppm to about 16,000 ppm of the composition. The free radical stabilizer may comprise from about 7000 ppm to about 16,000 ppm of the composition. The free radical stabilizer may comprise from about 14,000 ppm to about 16,000 ppm of the composition. The free radical stabilizer may comprise from about 5000 ppm to about 15,000 ppm, from about 7000 ppm to about 15,000 ppm of the composition, or from about 10,000 ppm to about 16,000 ppm of the composition. A free radical stabilizer may comprise about 5000 ppm, about 7000 ppm, about 8000 ppm, about 10,00 ppm, about 12,000 ppm, about 14,000 ppm, about 15,000 ppm, about 16,000 ppm, or more of the composition.

Anionic stabilizers that may be used include sulfur dioxide, and also include strong acids such as perchloric acid, hydrochloric acid, hydrobromic acid, toluenesulfonic acid, fluorosulfonic acid, phosphoric acid, ortho, meta, or para-phosphoric acid, trichloroacetic acid, and sulfuric acid. Generally speaking, the compositions comprise either sulfur dioxide or a strong acid anionic stabilizer, but not both, although both may be used in some aspects. In preferred aspects, the anionic stabilizer is sulfur dioxide.

In some aspects, the anionic stabilizer is used in an amount of at least about 20 ppm, and more preferably at least about 25 ppm, and even more preferably at least about 50 ppm of the composition. The amount of anionic stabilizer is preferably less than about 200 ppm, more preferably less than about 150 ppm, and even more preferably less than about 200 ppm. When sulfur dioxide is used, the sulfur dioxide may comprise from about 2 to about 500 ppm, from about 5 to about 300 ppm, from about 10 ppm to about 200 ppm, or from about 5 ppm to about 50 ppm of the composition. When a strong acid is used, the strong acid may comprise from about 1 ppm to about 250 ppm, from about 3 ppm to about 150 ppm, from about 4 ppm to about 100 ppm, from about 5 ppm to about 50 ppm, from about 10 ppm to about 40 ppm, from about 20 ppm to about 40 ppm, or from about 30 ppm to about 40 ppm of the composition.

The composition may optionally include a polymerization accelerator. The polymerization accelerator is preferably mixed together with the stabilized cyanoacrylate monomers. Suitable polymerization accelerators include, but are not limited to calixarenes and oxacalixarenes, silacrowns, crown ethers, cyclodextrin and its derivatives, polyethers, aliphatic alcohol, various aliphatic carboxylic acid esters, benzoyl peroxide, amine compounds such as triethyl amine, diethyl amine, butyl amine, isopropyl amine, tributyl amine, N,N-dimethyl aniline, N,N-diethyl aniline, N,N-dimethyl-p-toluidine, N,N-dimethyl-m-toluidine, N,N-dimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts such as alkylammonium salts, amide-bonded ammonium salts, ester-bonded ammonium salts, salts and alkylimidazolinium salts, cyclosulfur compounds and derivatives, and polyalkylene oxides and derivatives.

Crown ethers are preferred polymerization accelerators. Suitable crown ethers include, but are not limited to, 15-crown-5; 18-crown-6; dibenzo-18-crown-6; tribenzo-18-crown-6; dicyclohexyl-18-crown-6; benzo-15-crown-5; dibenzo-24-crown-8; dibenzo-30-crown-10; asym-dibenzo-22-crown-6; dimethylsila-11-crown-4; dimethylsila-14-crown-5; dimethylsila-17-crown-6; dibenzo-14-crown-4; dicyclohexyl-24-crown-8; asym-dibenzo-22-crown-6; cyclohexyl-12-crown-4; 1,2-decalyl-15-crown-5; 1,2-naphtho-15-crown-5; 3,4,5-naphthyl-16-crown-5; 1,2-methylbenzo-18-crown-6; 1,2-methylbenzo-5,6-methylbenzo-18-crown-6; 1,2-t-butyl-18-crown-6, 1,2-vinylbenzo-15-crown-5;1,2-vinylbenzo-18-crown-6; 1,24-butyl-cyclohexyl-18-crown-6; and 1,2-benzo-1,4-benzo-5-oxygen-20-crown-7. In preferred aspects, the polymerization accelerator is 18-crown-6.

The composition may comprise from about 10 ppm to about 6000 ppm of the polymerization accelerator. In some aspects, embodiments, the polymerization comprises from of about 40 ppm-5000 ppm, from about 60 ppm-4000 ppm, from about 100 to about 1000 ppm, from about 500 to about 1500 ppm, or from about 1000 to about 2000 ppm of the composition.

In some aspects, the compositions optionally include a thickener. Suitable thickening agents include polycyanoacrylate, a partial polymer of cyanoacrylate (for example, a partial polymer of the cyanoacrylate monomers that comprise the composition), polycaprolactone, copolymers of alkylacrylate and vinyl acetate, polyalkyl methacrylates, polyalkyl acrylates, lactic-glycolic acid copolymers, lactic acid-caprolactone copolymers, polyorthoesters, copolymers of alkyl methacrylates and butadiene, polyoxalates, and triblock copolymers of polyoxypropylene flanked by two hydrophilic chains of polyoxyethylene. In some aspects, t thickening agent may comprise a triblock copolymer of polyoxyalkylene as disclosed in U.S. Pat. No. 8,293,838. Preferably, the thickening agent is miscible with the cyanoacrylate monomer composition at room temperature. Biocompatible thickening agents are preferred for use in the medical field.

In some aspects, the composition may optionally comprise a colorant, such as a dye, pigment, or pigment dye. Suitable dyes include derivatives of anthracene and other complex structures. These dyes include without limitation, 1-hydroxy-4-[4-methylphenylamino]-9,10 anthracenedione (D&C violet No. 2); 9-(o-carboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); 2-(1,3dihydro-3-oxo-5-sulfo-2H-indole-2-ylidine)-2,3-dihydro-3-oxo-1H-indole-5 sulfonic acid disodium salt (FD&C Blue No. 2); and 1,4-bis(4-methylanilino)anthracene-9,10-dione (D&C Green No. 6).

In some aspects, the composition may optionally comprise a plasticizer. The plasticizing agent preferably does not contain any moisture and should not adversely affect the stability of the cyanoacrylate compositions. Examples of suitable plasticizers include, but are not limited to, tributyl citrate (TBC), acetyl tributyl citrate (ATBC), dimethyl sebacate, diethylsebacate, triethyl phosphate, tri(2-ethyl-hexyl)phosphate, tri(p-cresyl) phosphate, diisodecyl adipate (DIDA), glyceryl triacetate, glyceryl tributyrate, dioctyl adipate (DICA), isopropyl myrisate, butyl sterate, lauric acid, trioctyl trimelliate, dioctyl glutatrate (DICG) and mixtures thereof. Tributyl citrate, diisodecyl adipate and acetyl tributyl citrate are preferred plasticizers used in an amount of from about 0% to 30%, from about 1% to about 20%, or from about 2% to about 10% of the composition.

The compositions comprise one or more wound healing accelerating agents. Vitamin K, vitamin K oxides, and derivatives of vitamin K and vitamin K oxides may be used as the wound healing accelerating agent. Vitamin K has been used in various applications, for example, to aid blood clotting, and also in cosmetic applications to assist in the reduction of under-eye bruises and swelling and to reduce skin wrinkles. Because vitamin K may be unstable for use in topical applications, vitamin K oxide may be used since it is believed that vitamin K oxides have enhanced stability and effectiveness in topical formulations. Vitamin k oxide may have additional advantages over vitamin K in terms of a faster action for dermal indications, stability to light and heat, and allergenicity.

Compared to the extensive applications of Vitamin K in treating blood vessel disorders, skin rash, connective tissue diseases, osteolysis, osteoporosis, chronic venous insufficiency manifestations, cellulite, and dermatological conditions associated with inflammation, as described in U.S. Pat. Nos. 5,510,391, 5,866,106, 6,605,667, 8,283,382, and 8,211,947 as well as in U.S. Publ. Nos. 20120184609, 20100130618, 20100324148, 20090234022, 20080220094, 20070025950, and 20060275229, the application of vitamin K oxide is limited. For example, U.S. Pat. No. 3,070,499 describes a parenteral aqueous solution of fat-soluble vitamin K1 oxide, which finds application in nutrition for preventing certain well known diseases. JP-05320039 describes a cosmetic composition comprising vitamin K1 oxide without specification of any use. U.S. Pat. No. 7,939,568 describes the use of vitamin K1 oxide for treating dermatological lesions such as spider veins, bruise, blotches on the face or purpura, but requires the vitamin K1 oxide be present in nano-sized lipidic particles.

In some aspects, the wound healing accelerating agent comprises a naphthoquinone 2,3-oxide as set forth in formula III, wherein $R_1$ is any alkyl or aromatic group, preferably a saturated or unsaturated alkyl chain, and $R_2$ is H or any alkyl or aromatic group. Each R substituent may be the same or different. The wound healing accelerating agent may comprise homolog or derivative of a naphthoquinone 2,3-oxide of formula III.

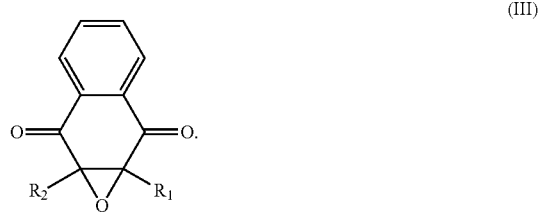

(III)

In some preferred aspects, the wound healing accelerating agent comprises 2-methyl-3-phytyl-1,4-naphthoquinone 2,3-oxide, also known as vitamin K1 oxide, 1a-methyl-7a-[(2E)-3,7,11,15-tetramethyl-2-hexadecen-1-yl]-1a,7a-dihydronaphtho[2,3-b]oxirene-2,7-dione, (2,3-epoxyphytyl) menaquinone, Vitamin K 2,3-epoxide, 2,3-epoxyphylloquinone, 2,3-epoxy-2,3-dihydro-2-methyl-3-phytyl-1,4-naphthoquinone, phylloquinone oxide, or any combination thereof. Other suitable derivatives of naphthoquinone 2,3-oxide or naphthoquinone include vitamin K2 oxide (menaquinone oxide), menadione epoxide, vitamin K2 (2-methyl-3-hexaprenyl-1,4-naphthoquinone; menaquinone), menadione (vitamin K3; 2-methyl-1,4-naphthoquinone), vitamin K4 (1,4-diacetoxy-2-methylnaphthalene), vitamin K5 (4-amino-2-methyl-1-naphthalenol), vitamin K6, vitamin K7 (3-methyl-4-amino-1-naphthol hydrochloride), dihydrovitamin K, menaquinone-4, menaquinone-6, menaquinone-7, menadiol, menadiol sodium diphosphate, menadiol diacetate, and menadoxime. The structure of vitamin K1 oxide is shown in Formula IV:

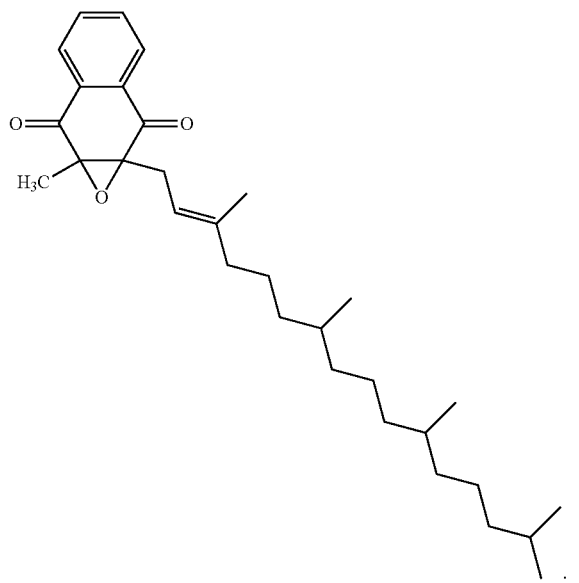

(IV)

The wound healing accelerating agent is preferably fully miscible with, and is homogenously mixed together with the stabilized cyanoacrylate monomer in the composition to form a homogeneous liquid cyanoacrylate monomer composition.

In some preferred aspects, a preferred wound healing accelerating agent comprises a naphthoquinone 2,3-oxide, including its derivatives and homologs, and including the more preferred vitamin K1 oxide, preferably comprises from about 0.01% to about 15% by weight of the composition. In some aspects, naphthoquinone 2,3-oxide, including the vitamin K1 oxide, comprises from about 0.02% to about 15%, from about 0.05% to about 12%, from about 1% to about 12%, from about 2% to about 10%, from about 5% to about 15%, from about 5% to about 12%, from about 7% to about 15%, from about 7% to about 12%, from about 9% to about 15%, from about 9% to about 12%, from about 10% to about 15%, from about 10% to about 13%, from about 10% to about 12%, from about 11% to about 15%, from about 11% to about 12%, or from about 12% to about 15% of the weight of the composition. The amount of naphthoquinone 2,3-oxide, including vitamin K1 oxide, incorporated into the cyanoacrylate composition may vary, for example, depending on the type of cyanoacrylate monomer. In some preferred aspects, a preferred wound healing accelerating agent comprises vitamin K, including the more preferred agents vitamin K1, vitamin K2, vitamin K3, Vitamin K4, and/or vitamin K5, preferably comprises from about 0.01% to about 15% by weight of the composition. In some aspects, vitamin K, including the more preferred agents vitamin K1, vitamin K2, vitamin K3, Vitamin K4, and/or vitamin K5, comprises from about 0.02% to about 15%, from about 0.05% to about 12%, from about 1% to about 12%, from about 2% to about 10%, from about 5% to about 15%, from about 5% to about 12%, from about 7% to about 15%, from about 7% to about 12%, from about 9% to about 15%, from about 9% to about 12%, from about 10% to about 15%, from about 10% to about 13%, from about 10% to about 12%, from about 11% to about 15%, from about 11% to about 12%, or from about 12% to about 15% of the weight of the composition. The amount of vitamin K, including the more preferred agents vitamin K1, vitamin K2, vitamin K3, Vitamin K4, and/or vitamin K5, incorporated into the cyanoacrylate composition may vary, for example, depending on the type of cyanoacrylate monomer.

In some aspects, the composition comprises 2-octyl cyanoacrylate, 0.5% by weight of vitamin K1 oxide, BHA and SO$_2$ as stabilizers, and 18-crown-6 crown ether as the accelerator. In some aspects, the composition comprises 2-octyl cyanoacrylate, 0.5% by weight of vitamin K1 oxide, and BHA and SO$_2$ as stabilizers. In some aspects, the composition comprises 2-octyl cyanoacrylate, 1.5% by weight of vitamin K1 oxide, BHA and SO$_2$ as stabilizers, and 18-crown-6 crown ether as the accelerator. In some aspects, the composition comprises 2-octyl cyanoacrylate, 1.5% by weight vitamin K1 oxide, and BHA and SO$_2$ as stabilizers. In some aspects, the composition comprises 2-octyl cyanoacrylate, 2.5% by weight of vitamin K1 oxide, BHA and SO$_2$ as stabilizers, 18-crown-6 crown ether as the accelerator. In some aspects, the composition comprises 2-octyl cyanoacrylate, 2.5% by weight of vitamin K1 oxide, and BHA and SO$_2$ as stabilizers. In some aspects, the composition comprises 2-octyl cyanoacrylate, 5% by weight of vitamin K1 oxide, and BHA and SO$_2$ as stabilizers, and 18-crown-6 crown ether as the accelerator. In some aspects, the composition comprises 2-octyl cyanoacrylate, 5% by weight of vitamin K1 oxide, and BHA and SO$_2$ as stabilizers. The amount of 2-octyl cyanoacrylate monomer, BHA and SO$_2$ stabilizers, and the 18-crown-6 crown ether, if present, may be according to any amount described or exemplified herein for each such component. Vitamin K1 may be substituted with any other vitamin K oxide.

In some aspects, the composition comprises n-butyl cyanoacrylate, 0.5% by weight of vitamin K1 oxide, BHA and $SO_2$ as stabilizers, and 18-crown-6 crown ether as the accelerator. In some aspects, the composition comprises n-butyl cyanoacrylate, 0.5% by weight of vitamin K1 oxide, and BHA and $SO_2$ as stabilizers. In some aspects, the composition comprises n-butyl cyanoacrylate, 1.5% by weight of vitamin K1 oxide, BHA and $SO_2$ as stabilizers, and 18-crown-6 crown ether as the accelerator. In some aspects, the composition comprises n-butyl cyanoacrylate, 1.5% by weight vitamin K1 oxide, and BHA and $SO_2$ as stabilizers. In some aspects, the composition comprises n-butyl cyanoacrylate, 2.5% by weight of vitamin K1 oxide, BHA and $SO_2$ as stabilizers, 18-crown-6 crown ether as the accelerator. In some aspects, the composition comprises n-butyl cyanoacrylate, 2.5% by weight of vitamin K1 oxide, and BHA and $SO_2$ as stabilizers. In some aspects, the composition comprises n-butyl cyanoacrylate, 5% by weight of vitamin K1 oxide, and BHA and $SO_2$ as stabilizers, and 18-crown-6 crown ether as the accelerator. In some aspects, the composition comprises n-butyl cyanoacrylate, 5% by weight of vitamin K1 oxide, and BHA and $SO_2$ as stabilizers. The amount of n-butyl cyanoacrylate monomer, BHA and $SO_2$ stabilizers, and the 18-crown-6 crown ether, if present, may be according to any amount described or exemplified herein for each such component. Vitamin K1 may be substituted with any other vitamin K oxide.

In some aspects, the composition comprises a mixture of 2-octyl cyanoacrylate and n-butyl cyanoacrylate, 0.5% by weight of vitamin K1 oxide, BHA and $SO_2$ as stabilizers, and 18-crown-6 crown ether as the accelerator. In some aspects, the composition comprises a mixture of 2-octyl cyanoacrylate and n-butyl cyanoacrylate, 0.5% by weight of vitamin K1 oxide, and BHA and $SO_2$ as stabilizers. In some aspects, the composition comprises a mixture of 2-octyl cyanoacrylate and n-butyl cyanoacrylate, 1.5% by weight of vitamin K1 oxide, BHA and $SO_2$ as stabilizers, and 18-crown-6 crown ether as the accelerator. In some aspects, the composition comprises a mixture of 2-octyl cyanoacrylate and n-butyl cyanoacrylate, 1.5% by weight vitamin K1 oxide, and BHA and $SO_2$ as stabilizers. In some aspects, the composition comprises a mixture of 2-octyl cyanoacrylate and n-butyl cyanoacrylate, 2.5% by weight of vitamin K1 oxide, BHA and $SO_2$ as stabilizers, 18-crown-6 crown ether as the accelerator. In some aspects, the composition comprises a mixture of 2-octyl cyanoacrylate and n-butyl cyanoacrylate, 2.5% by weight of vitamin K1 oxide, and BHA and $SO_2$ as stabilizers. In some aspects, the composition comprises a mixture of 2-octyl cyanoacrylate and n-butyl cyanoacrylate, 5% by weight of vitamin K1 oxide, and BHA and $SO_2$ as stabilizers, and 18-crown-6 crown ether as the accelerator. In some aspects, the composition comprises a mixture of 2-octyl cyanoacrylate and n-butyl cyanoacrylate, 5% by weight of vitamin K1 oxide, and BHA and $SO_2$ as stabilizers. Vitamin K1 may be substituted with any other vitamin K oxide. The amount of a mixture of 2-octyl cyanoacrylate and n-butyl cyanoacrylate monomer, BHA and $SO_2$ stabilizers, and the 18-crown-6 crown ether, if present, may be according to any amount described or exemplified herein for each such component. The ratio of 2-octyl cyanoacrylate to n-butyl cyanoacrylate in the monomer mixture can be any suitable percent ratio, for example (2-octyl:n-butyl): 5:95, 10:90, 15:85, 20:80, 25:75, 30:70, 35:65, 40:60, 45:55, 50:50, 55:45, 60:40, 65:35, 70:30. 75:25, 80:20, 85:15, 90:10, or 95:5.

The compositions may optionally include other medicaments and skin beneficial ingredients, such as vitamin C, vitamin A, folic acid, vitamin D, vitamin E, amino acids, analgesics, anti-itch agents, skin penetration enhancers, fibrin, aminocaproic acid, tranexamic acid, aprotin, fibrinogen-containing agents, collagen, collagen-containing agents, anti-acne agents, moisturizers, glycerin, propylene glycol, polyethylene glycol, hyaluronic acid, chondroitin sulfate, elastin, antioxidants, and other skin-improvement agents.

In some aspects, the compositions may be treated with basic polymers or copolymers to reduce the amount of contaminants and extraneous additives in the cyanoacrylate monomer, but this can lead to several problems including premature polymerization. Some basic polymers or copolymers are not soluble in cyanoacrylate but are mixed with the monomer adhesive in mutual contact until the adhesive is destabilized. In order to achieve the mutual contact, such polymers or copolymers are mixed with the cyanoacrylate monomer under vacuum for a minimum of 3 hours, which may remove possible acid residues to destabilize the adhesive. The solid powder of such polymer is then removed from cyanoacrylate adhesive by filtering, for example, through a 0.2 µm filter.

The compositions may be filtered to reduce the bioburden level of the composition and remove any immiscible impurity. The size of the primary filter used may be in the range of about 0.01 to about 0.8 µm, preferably in the range of about 0.01 to about 0.6 µm, and more preferably in the range of about 0.03 to about 0.6 µm. The size of the additional filters used may be in the range of about 1 to about 200 µm, preferably in the range of about 1 to about 150 µm, and more preferably in the range of about 1 to about 100 µm.

The compositions are preferably sterilized. Thus, the mixture of the cyanoacrylate monomers, stabilizers, wound healing accelerating agent, and other agents (polymerization accelerator, plasticizer, thickener, dye, etc.) is preferably sterilized. Sterilization may comprise chemical, physical, or radiation sterilization. Non-limiting examples of chemical sterilization include treatment of the composition with ethylene oxide and/or hydrogen peroxide. Examples of physical methods include, but are not limited to, sterilization by heat (dry or moist) or retort canning. Examples of radiation include, but are not limited to, gamma irradiation, electron beam irradiation, X-ray irradiation, ultraviolet, and microwave irradiation. Ionizing radiation such as gamma, electron beam (E-beam), and x-ray radiation are preferred. The compositions may be packaged into a suitable applicator prior to sterilization. In some aspects, sterilization modalities may be combined, including sequential sterilization with ethylene oxide then ionizing radiation.

When sterilizing the composition using E-beam irradiation, the dose is sufficient enough to sterilize the adhesive compositions without inducing premature polymerization, for example, typically in the range of from about 5 kGy to 50 kGy, and more preferably from about 5 kGy to 25 kGy. E-beam irradiation is preferably conducted at ambient atmosphere conditions and the exposure time to the irradiation is preferably within 60 seconds. The beam power may range from about 2 KW to about 30 KW, preferably about 5 KW to about 20 KW, and more preferably about 10 KW to about 20 KW. The beam energy may range from 1 million to 10 million electron volts (MeV), preferably 3 MeV to 10 MeV, and more preferably 5 MeV to 10 MeV.

When sterilizing the composition using Gamma irradiation the dose is sufficient enough to sterilize the adhesive compositions without inducing premature polymerization, for example, typically in the range of from about 5 kGy to about 40 kGy, preferably in the range of about 5 kGy to about 30 kGy, more preferably about 5 kGy to about 25 kGy, and most preferably about 5 kGy to about 20 kGy.

When sterilizing the composition using x-ray irradiation the dose is sufficient enough to sterilize the adhesive compositions without inducing premature polymerization, for example, typically in the range of from about about 5 kGy to about 40 kGy, preferably in the range of about 5 kGy to about 30 kGy, more preferably about 5 kGy to about 25 kGy, and most preferably about 5 kGy to about 20 kGy. The X-ray energy may range from 1 million to 10 million electron volts (MeV), preferably 3 MeV to 10 MeV, and more preferably 3 to 7.5 MeV.

The composition is preferably sterilized to provide a Sterility Assurance Level (SAL) of at least $10^{-3}$. This means that the probability of a single unit being non-sterile after sterilization is 1 in 1000. In more preferred embodiments, the sterility assurance level may be at least $10^{-4}$, $10^{-5}$, or $10^{-6}$. After sterilizing the inventive cyanoacrylate adhesive compositions, their sterility levels were analyzed by Bacteriostasis and Fungistasis tests. After testing with challenging microorganisms such as *Bacillus subtilis*, *Candida albicans*, and *Aspergillus niger*, no growth of the microorganisms was observed, indicating the sterility of the inventive compositions.

The compositions, after irradiation sterilization, preferably set within about 5 seconds to about 120 seconds, preferably within about 5 seconds to 100 seconds, and more preferably within about 10 to about 100 seconds. The compositions, after irradiation sterilization, preferably set in about 60 seconds or less.

Irradiation sterilization was observed to have a drastic and disparate effect on cyanoacrylate compositions containing different amounts of naphthoquinone 2,3-oxide, which were stabilized with different amounts of free radical and anionic stabilizers. Table 1 shows the viscosity of some cyanoacrylate compositions with different amounts of naphthoquinone 2,3-oxide and stabilizers, before and after irradiation sterilization. As demonstrated in Table 1, some cyanoacrylate-Vitamin K1 oxide compositions were cured upon irradiation sterilization, but some preferred compositions showed essentially no change or a slight increase in viscosity upon sterilization, indicating a negligible effect of irradiation sterilization on the inventive adhesive compositions.

TABLE 1

Viscosity of the cyanoacrylate adhesive compositions containing Vitamin K1 oxide before and after sterilization, which are stabilized with different amounts of free radical and anionic stabilizers.

| Sample (Formulation) | Amount of Vitamin K1 oxide | Average Viscosity (cp) | |
|---|---|---|---|
| | | Before Sterilization | After sterilization |
| 101712-1 (Example 2) | 0.5% | 6.68 | 7.74 |
| 112712-1 (OCA, 0.5% Vitamin K1 oxide, <10 ppm SO$_2$, <0.2% BHA) | 0.5% | 7.11 | Cured upon sterilization |
| 112712-2 (OCA, 1% Vitamin K1 oxide, <10 ppm SO$_2$, <0.2% BHA) | 1% | 5.93 | Cured upon sterilization |
| 112712-4 (OCA, 1% vitamin K1 oxide, 10 ppm SO$_2$, <0.2% BHA) | 1% | 6.34 | 19.6 |
| 112712-5 (Example 6) | 1% | 7.38 | Cured upon sterilization |
| 112812-1 (Example 9) | 1% | 7.61 | 15.1 |
| 112812-2 (OCA, 1% vitamin K1 oxide, <10 ppm SO$_2$, 0.3% BHA) | 1% | 7.55 | Cured upon sterilization |
| 112912-3 (Example 8) | 0.5% | 7.23 | Cured upon sterilization |
| 112912-4 (OCA, 0.5% vitamin K1 oxide, <10 ppm SO$_2$, 0.5% BHA) | 0.5% | 7.59 | Cured upon sterilization |
| 101812-1 (Example 4) | 1% | 6.27 | 6.98 |

Shortly after sterilization (e.g., by irradiation or physical or chemical sterilization), the composition may have a viscosity in the range of from about 3 centipoise (cPs) to about 100 cPs. In some aspects, the composition may have a viscosity in the range of from about 3 cPs to about 50 cPs, from about 3 cPs to about 20 cPs, from about 3 cPs to about 10 cPs, from about 4 cPs to about 15 cPs, from about 5 cPs to about 10 cPs, from about 5 cPs to about 8 cPs, from about 5 cPs to about 9 cPs, from about 5 cPs to about 100 cPs, from about 5 cPs to about 50 cPs, from about 5 cPs to about 20 cPs, from about 5 cPs to about 15 cPs, from about 10 cPs to about 20 cPs, from about 10 cPs to about 25 cPs, from about 6 cPs to about 7 cPs, from about 6 cPs to about 8 cPs, from about 6 cPS to about 9 cPs, or from about 6 cPs to about 10 cPs.

Preferably, the viscosity of the composition does not substantially increase upon sterilization (e.g., by irradiation or physical or chemical sterilization). For example, it is preferred that the viscosity of the composition before sterilization is substantially the same as the viscosity of the composition shortly after sterilization (and before extended shelf storage of the sterilized composition). After sterilization and before extended shelf storage, the viscosity of the cyanoacrylate composition may change, including an increase or decrease. The change in viscosity of the cyanoacrylate compositions after the sterilization and before extended shelf storage, may vary, for example, depending on the original viscosity and the presence of additives such as a polymerization accelerator, the amount of the wound healing accelerating agent, and/or the amount or type of stabilizers. The increase in viscosity of the composition after sterilization is preferably within about 1% to about 200%, more preferably within about 1% to about 80%, and more preferably within about 1% to about 60% of the initial, pre-sterilization viscosity of the composition. In some embodiments, the viscosity of the composition after sterilization is within about 5% to about 300% of the initial, pre-sterilization viscosity of the composition. After sterilization and before extended shelf storage, the viscosity may change about 5% to about 10%, about 5% to about 15%, about 5% to about 20%, about 7% to about 10%, about 7% to about 15%, about 8% to about 12%, about 8% to about 15%, about 8% to about 20%, about 10% to about 100%, about 10% to about 80%, about 10% to about 60%, about 10% to about 40%, about 10% to about 30%, about 10% to about 20%, about 20% to about 100%, about 20% to about 60%, about 20% to about 50%, about 20% to about 40%, about 20% to about 30%, about 30% to about 300%, about 30% to about 200%, about 30% to about 150%, about 30% to about 100%, about 30% to about 50%, about 40% to about 300%, about 40% to about 200%, about 40% to about 150%, about 40% to about 100%, about 40% to about 80%, about 40% to about 80%, about 50% to about 300%, about 50% to about 200%, about 50% to about 150%, about 50% to about 100%, about 50% to about 90%, about 50% to about 80%, about 60% to about 200%, about 60% to about 100%, about 70% to about 200%, about 70% to about 100%, about 80% to about 100% of the initial, pre-sterilization viscosity.

In some aspects, the compositions comprising naphthoquinone 2,3-oxide and its homologs or derivatives, including vitamin K1 oxide, or vitamin K2, which do not include any thickening agent, have a viscosity of from about 3 cps to about 100 cps, preferably from about 3 cps to about 50 cps, more preferably from about 3 cps to about 20 cps, and more preferably from about 3 cps to about 15 cps following irradiation sterilization, but prior to prolonged shelf storage. Following irradiation sterilization, but prior to prolonged shelf storage, the viscosity of the composition may be less than about 400 cPs, less than about 300 cPs, less than about 200 cPs, less than about 100 cPs, less than about 50 cPs, less than about 25 cPs, less than about 20 cPs, less than about 15 cPs, less than about 10cPs, or less than about 8 cPs. Following irradiation sterilization, but prior to prolonged shelf storage, the viscosity of the composition may range from about 3 cPs to about 100 cPs, from about 3 cPs to about 50 cPs, from about 3 cPs to about 20 cPs, from about 3 cPs to about 10 cPs, from about 4 cPs to about 15 cPs, from about 5 cPs to about 10 cPs, from about 5 cPs to about 7 cPs, from about 5 cPs to about 9 cPs, from about 5 cPs to about 8 cPs, from about 5 cPs to about 100 cPs, from about 5 cPs to about 50 cPs, from about 5 cPs to about 20 cPs, from about 5 cPs to about 15 cPs, from about 10 cPs to about 20 cPs, from about 10 cPs to about 25 cPs, from about 6 cPs to about 7 cPs, from about 6 cPs to about 8 cPs, from about 6 cPs to about 10 cPs, from about 6 cPs to about 14 cPs, from about 7 cPs to about 12 cPs, from about 7 cPs to about 10 cPs, from about 10 cPs to about 60 cPs, from about 10 cPs to about 15 cPs, from about 15 cPs to about 20 cPs, from about 15 cPs to about 25 cPs, from about 15 cPs to about 30 cPs, from about 10 cPs to about 15 cPs, from about 10 cPs to about 20 cPs, from about 20 cPs to about 25 cPs, from about 20 cPs to about 30 cPs, from about 25 cPs to about 50 cPs, from about 25 cPs to about 75 cPs, or from about 25 cPs to about 30 cPs.

During shelf storage, the sterilized compositions may further change in viscosity. The viscosity may increase or decrease, although the viscosity may tend to increase.

It is preferred that the compositions have a shelf-life of at least one year under ambient conditions, and more preferably that the compositions have a shelf-life of at least two years under ambient conditions. An increased shelf-life beyond this provides increased economic advantages to both the manufacturer and the consumer, and so the compositions may have a shelf-life of greater than two years. Ambient conditions include storage at approximately room temperature or less, without substantial humidity. The shelf-life may be assessed as a function of the extent of viscosity changes and degradation of the composition, to the extent that the composition cannot be used in the manner and for the purpose for which they were intended. Thus, while some polymerization or thickening of the composition may occur, such as can be measured by changes in viscosity of the composition, such change is not so extensive as to destroy or significantly impair the usefulness of the composition. Prolonged or extended shelf storage or shelf life are used interchangeably, and include a shelf-life of at least about 12 months, preferably at least about 18 months, and more preferably at least about 24 months.

Shelf life is, in part, reflected in post-sterilization viscosity changes. For example, the post-sterilization viscosity changes described herein may be measured at least about six months, at least about one year, at least about one and one half years, or at least about two years following sterilization. The period of time as measured may elapse in real time, or may be approximated via an accelerated aging study. The American Society for Testing and Materials (ASTM) has established standard advance aging assays for investigating the aging of sterilized medical device packages. One such standard is the ASTM F1980-02 Standard Guide for Accelerated Aging of Sterile Medical Device Packages. The F1980-02 standard has been superseded by the ASTM F1980-07 (2011) Standard Guide for Accelerated Aging of Sterile Barrier Systems for Medical Devices. Either standard accelerated aging test may be used to approximate two years of real time aging of the compositions. In general, the compositions undergoing an accelerated aging test are warehoused in an oven at 80° C. (dry heat) for a period of 12 days (F1980-02) or for a period of 13 days (F1980-07), which respectively approximate two years of shelf life at ordinary/ambient storage temperatures and atmospheric conditions. In some aspects, the compositions undergoing an accelerated aging test are warehoused in an oven at 80° C. (dry heat) for a period of 6 days (F1980-02) or for a period of 6.5 days (F1980-07), which respectively approximate one year of shelf life at ordinary storage temperatures and atmospheric conditions.

Following about one year of shelf storage, the viscosity of the sterilized composition preferably does not increase more than about 600% of the pre-sterilization viscosity. Following about one year of shelf storage, the viscosity of the sterilized composition preferably does not increase more than about 500% of the pre-sterilization viscosity. Following about one year of shelf storage, the viscosity of the sterilized composition preferably does not increase more than about 450% of the pre-sterilization viscosity. Following about one year of shelf storage, the viscosity of the sterilized composition preferably does not increase more than about 400% of the pre-sterilization viscosity. Following about one year of shelf storage, the viscosity of the sterilized composition preferably does not increase more than about 350% of the pre-sterilization viscosity. Following about one year of shelf storage, the viscosity of the sterilized composition preferably does not increase more than about 300% of the pre-sterilization viscosity. Following about one year of shelf storage, the viscosity of the sterilized composition preferably does not increase more than about 250% of the pre-sterilization viscosity. Following about one year of shelf storage, the viscosity of the sterilized composition preferably does not increase more than about 200% of the pre-sterilization viscosity. Following about one year of shelf storage, the viscosity of the sterilized composition preferably does not increase more than about 150% of the pre-sterilization viscosity.

Following about two years of shelf storage, the viscosity of the sterilized composition preferably does not increase more than about 1000% of the pre-sterilization viscosity. Following about two years of shelf storage, the viscosity of the sterilized composition preferably does not increase more than about 950% of the pre-sterilization viscosity. Following about two years of shelf storage, the viscosity of the sterilized composition preferably does not increase more than about 900% of the pre-sterilization viscosity. Following about two years of shelf storage, the viscosity of the sterilized composition preferably does not increase more than about 850% of the pre-sterilization viscosity. Following about two years of shelf storage, the viscosity of the sterilized composition preferably does not increase more than about 800% of the pre-sterilization viscosity. Following about two years of shelf storage, the viscosity of the sterilized composition preferably does not increase more than about 750% of the pre-sterilization viscosity. Following about two years of shelf storage, the viscosity of the sterilized composition preferably does not increase more than about 700% of the pre-sterilization viscosity. Following about two years of shelf storage, the viscosity of the sterilized composition preferably does not increase more than about 600% of the pre-sterilization viscosity. Following about two years of shelf storage, the viscosity of the sterilized composition preferably does not increase more than about 500% of the pre-sterilization viscosity. Following about two years of shelf storage, the viscosity of the sterilized composition preferably does not increase more than about 450% of the pre-sterilization viscosity. Following about two years of shelf storage, the viscosity of the sterilized composition preferably does not increase more than about 400% of the pre-sterilization viscosity. Following about two years of shelf storage, the viscosity of the sterilized composition preferably does not increase more than about 350% of the pre-sterilization viscosity. Following about two years of shelf storage, the viscosity of the sterilized composition preferably does not increase more than about 300% of the pre-sterilization viscosity. Following about two years of shelf storage, the viscosity of the sterilized composition preferably does not increase more than about 250% of the pre-sterilization viscosity. Following about two years of shelf storage, the viscosity of the sterilized composition preferably does not increase more than about 200% of the pre-sterilization viscosity.

To evaluate the shelf storage capacity of the compositions after sterilization, an accelerated aging test was performed. The accelerated aging test was performed in an oven at 80° C. for a period of 13 days (ASTM F1980-07). Based on calculations, 13 days accelerated aging at 80° C. is equal to 2 years of shelf life, and 1 day of accelerated aging at 80° C. is equal to 56 days.

The viscosity of the compositions was measured by the Brookfield DV-II+ viscometer. The spindle and cup were cleaned with acetone after each measurement. About 0.5 ml of the composition was put into the cup and the cup was brought into position and slowly secured with the retaining arm. The motor was turned on after the sample was equilibrated in the cup. The viscosity of each composition was measured in triplicate. Any residue was removed with acetone prior to next sample measurement.

TABLE 2

Viscosity of the cyanoacrylate adhesive compositions containing Vitamin K1 oxide sterilized by Gamma sterilization at different intervals of the accelerated aging at 80° C.

| Composition | Viscosity (cps) at different intervals of the accelerated aging at 80° C. | | | | |
| --- | --- | --- | --- | --- | --- |
| | Day 0 | Day 3 | Day 6 | Day 10 | Day 13 |
| 101712-1 | 7.74 | 15.4 | 21.0 | 46.0 | 89.0 |
| 112712-4 | Cured at day 3 of the accelerated aging at 80° C. | | | | |
| 112812-1 | Cured at day 6 of the accelerated aging at 80° C. | | | | |
| 101812-1 | 6.98 | 7.97 | 8.91 | 11.2 | 14.5 |

The stability of the aged samples was confirmed by viscosity tests. The viscosity of the cyanoacrylate adhesive compositions slightly increased as the accelerated aging proceeded, indicating very little premature polymerization of the cyanoacrylate monomers occurred upon sterilization. Table 2 summarizes the viscosity of the cyanoacrylate adhesive compositions containing Vitamin K1 oxide sterilized by Gamma sterilization at different intervals of the accelerated aging at 80° C. The average viscosity of the compositions 101812-1 and 101712-1 at day 13 of the accelerated aging at 80° C. was 14.5 and 89.0 centipoise (cps), respectively. On the other hand, compositions 112712-4 and 112812-1 were cured at day 3 and day 6 of the accelerated aging at 80° C., respectively, indicating such sterilized compositions could not provide a shelf life of 2 years.

Cyanoacrylate monomer compositions comprising wound healing accelerating agents, for example, naphthoquinone 2,3-oxides, including vitamin K1 oxide, or a vitamin K2 oxide, are suitable for use in a variety of wound closure applications. Preferably, such compositions may be used in a surgical setting to promote the healing of surgical incisions and/or open wounds. The compositions may also be used to treat and close chronic wounds or those which are resistant to healing. Thus, the compositions may both close wounds and accelerate their healing. It is believed that although Vitamin K oxides have been used to treat non-open wounds such as purpura and bruises and in promoting blood clotting and skin care, Vitamin K oxides have not been used as a wound healing agent for open wounds. It is believed that incorporation of Vitamin K oxides into cyanoacrylate monomer adhesive compositions for promoting wound healing of surgical incisions and open wound has never been investigated.

The cyanoacrylate compositions comprising a wound healing accelerator may be used to close and enhance the healing of any open wounds, including surgical incisions, including but are not limited to, punctures from minimally invasive surgery, simple, thoroughly cleansed trauma, lacerations, superficial wounds such as abrasions, skin tears, and blisters, chafed skin or skin continuously exposed to moisture, skins damaged by poison ivy, and stage 1 and stage 2 pressure ulcers, and bed sores. The compositions may also be used to secure catheter devices to the skin and to cover and protect catheter entry sites, which include, but are not limited to, intravenous catheters, central venous catheters, and epidural catheters. Application of cyanoacrylate compositions onto catheters enhances stability of catheters and reduces migration, and dislodgement of catheters, and positioning of a catheter in the vein.

Thus, for example, the compositions may be applied to a wound and allowed to cure on the wound, thereby closing the wound and accelerating healing of the wound. For example, after topically applying the composition to a wound or surgical incision, the liquid cyanoacrylate monomers polymerize and then cure to form a polymer films with tissue growth-stimulating, antimicrobial and mechanical barrier properties. By incorporating naphthoquinone 2,3-oxides or derivatives thereof in the composition, the oxides become incorporated into the polymer film, and slowly leach from the film in order to enhance the speed of wound healing. Wound healing includes, for example, permanent closure of the wound by the body.

The naphthoquinone 2,3-oxides, including vitamin K1 oxides, or vitamin K2 oxides, enhance the rate and efficiency of permanent wound closure by the body (wound healing). For example, a wound closed by a cyanoacrylate composition described or exemplified herein will heal at a rate of about 1.5 to about 10 times faster than the wound would heal if closed by a cyanoacrylate composition that did not include any naphthoquinone 2,3-oxides or their derivatives, including vitamin K1 oxides or vitamin K2 oxides, or other related wound healing accelerating agent. A wound closed by a cyanoacrylate composition described or exemplified herein will heal at a rate of about 0.5, about 1, about 2, about 3, about 4, about 5, about 6, about 7, about 8, about 9, or about 10 times faster than the wound would heal if closed by a cyanoacrylate composition that did not include any naphthoquinone 2,3-oxides, or their derivatives including vitamin K1 oxides, vitamin K2 oxides, vitamin K3 oxides, vitamin K4 oxides, vitamin K5 oxides, vitamin K6 oxides, vitamin K7 oxides or other related wound healing accelerating agent.

The invention also features kits for storing and/or applying the sterilized cyanoacrylate adhesive compositions. The kits include the composition in a container. The composition preferably is sterilized in the container.

The container may comprise an applicator. The applicator may be used to apply the composition to a surface, for example, a surface of the skin or to the surface of a catheter inserted into the skin. The applicators may comprise a swab, brush, sponge, or foam tip, or any suitable surface or tip to dispense the composition from the container. The applicator may comprise a spray nozzle. The kits may further contain other appropriate practical elements to suit specific uses, including but not limited to surgical tools, other medicaments and directions for application. For example, the kits may comprise instructions for using the composition in a method for closing a wound or in a method for securing a catheter in place. Individual containers or applicators can be packaged separately to maintain sterile conditions. For example, each applicator can be packaged in plastic or any other suitable enclosing material. Multiple applicators can then be packaged in a box for shipping.

The materials out of which the container is fabricated are preferably capable of withstanding irradiation without damaging or weakening the structural integrity of the container due to radiation exposure. In some preferred aspects, the container provides a barrier to gas and moisture so that it further protects the cyanoacrylate monomer compositions from moisture that can induce premature polymerization of the monomers. Containers may comprise a vial, pouch, syringe, ampoule, or bottle. The container may include for example, from about 0.1 mL to about 10 mL, preferably from about 0.1 mL to about 5 mL, and more preferably from about 0.2 mL to about 5 mL of the composition.

The container may comprise a foil seal, which may comprise one or more layers. The foil seal may be affixed, such as heat sealed, to the container body after the adhesive is filled into the container. A multi-layer foil seal may comprise an inner layer, middle layers, and an outer layer, and the inner layer may comprise a material with gas and moisture barrier properties.

The container may comprise multiple layers of different materials, including polymers and metal. Preferably, the container is fabricated from an acrylonitrile copolymer. In some preferred aspects, the container comprises an inner layer comprising an acrylonitrile copolymer and an outer layer comprising polypropylene or aluminum. Acrylonitrile copolymer provides high barrier properties which ensure the stability of the cyanoacrylate adhesive product stored therein. The exceptional barrier properties offered by acrylonitrile copolymer make them an ideal inner layer material for use in construction of package bodies in accordance with the present invention. Acrylonitrile copolymer offer a high barrier to oxygen at all levels of relative humidity. This ensures that a consistently high barrier to oxygen is maintained, regardless of the humidity of the surrounding environment. In addition, the water vapor barrier properties of acrylonitrile copolymer are comparable to other plastic packaging materials and are ultimately enhanced by the outer layer secured thereto in accordance with the present invention.

The container may comprise a single-use container or a multiple-use container where it is desired to maintain a high degree of prolonged sterility and stability of the composition against microbial action despite loss of initial sterility upon first use of the composition. The single-use container may be a spray applicator, where said adhesive compositions can be sprayed onto open wounds without having to make the applicator/container to be in direct contact with the local open wounds.

The compositions are suitable for wound closure applications. When applied to a wound, the compositions accelerate wound closure and healing, for example, relative to a wound of the same type in which the compositions were not applied. Thus, the invention also features methods for closing a wound on a subject in need thereof.

In general, the methods comprise applying the composition to a wound of a subject in need thereof, and allowing the composition to cure over the wound, thereby closing the wound. The composition preferably is applied to the skin surface, including the skin surfaces that surround or otherwise border the wound. In this way, the composition, when cured, bridges the surrounding skin surfaces together and seals the wound. The composition may be allowed to remain on the wound for a period of time sufficient for the wound to heal or at least permanently close. The composition may be re-applied after a period of time, for example, to maintain a closure of the wound for as long as it takes for the wound to heal. Application and re-application may be at the direction of a medical practitioner.

The methods may be used to close any wound. For example, a wound may comprise any skin or dermal tissue trauma, including without limitation a surgical incision, cut, scrape, bite, puncture, laceration, abrasion, tear, blister, or rash. A rash may include, for example, poison ivy or poison oak or poison sumac. The wound may comprise a skin ulcer. The skin ulcer may comprise a pressure ulcer. The pressure ulcer may comprise a bed sore. Thus, for example, the wound may comprise a bed sore.

The wound may also comprise a catheter entry point, for example, for a catheter inserted into the skin. Thus, the methods may also comprise securing a catheter inserted into the skin of a subject in place. For example, the methods may comprise contacting a skin surface at or at least proximal to the catheter entry point with the composition, then contacting the composition with a surface of the catheter, and allowing the composition to cure between the catheter surface and the skin, thereby securing the catheter in place and at the same time sealing off the catheter entry wound. In some alternative aspects, the method may comprise contacting a surface of the catheter with the composition, then contacting the composition with a surface of the skin at or at least proximal to the catheter entry point, and allowing the composition to cure between the catheter surface and the skin, thereby securing the catheter in place and at the same time sealing off the catheter entry wound. In some alternative aspects, the method may comprise contacting a surface of the catheter and contacting a surface of the skin at or at least proximal to the catheter entry point with the composition, contacting each applied amount of the composition with each other, and allowing the composition to cure between the catheter surface and the skin, thereby securing the catheter in place and at the same time sealing off the catheter entry wound.

The following examples are provided to describe the invention in greater detail. They are intended to illustrate, not to limit, the invention.

Example 1

In a three neck round bottom flask equipped with a magnetic stir bar, 5.2 g of vitamin K1 oxide was mixed with 98.8 g of the activated 2-octyl cyanoacrylate that includes 0.719 g of butylated hydroxyanisole, 0.468 g of $SO_2$ solution (0.579%), 6 mg of DC violet #2, and 20.8 mg of 18-crown-6 at room temperature. Vitamin K1 oxide was well-miscible with 2-octyl cyanoacrylate. The viscosity and set time of the composition were 7.65 cps and 27.5 seconds, respectively.

Example 2

114.7 g of the activated 2-octyl cyanoacrylate with 0.654 g of butylated hydroxyanisole, 2.1 mg of $SO_2$, and 0.9 mg of DC violet #2 was mixed with 0.574 g of vitamin K1 oxide in a three neck round bottom flask equipped with a magnetic stir bar, to which 23 mg of 18-crown-6 was added. Vitamin K1 oxide is miscible with 2-octyl cyanoacrylate composition right away. The composition was sterilized by Gamma irradiation at the dose range of 9.4-11.0 kGy. Upon sterilization, the increase in viscosity of the composition is 1.06 cps. The average set time of the composition after sterilization was 27.5 seconds.

Example 3

In a three neck round bottom flask equipped with a magnetic stir bar, 0.7 g of 2-methyl-1,4-naphthoquinone was mixed with 232.6 g of the activated 2-octyl cyanoacrylate that includes 1.676 g of butylated hydroxyanisole, 6 mg of $SO_2$, 20.4 mg of DC violet #2, and 46.7 mg of 18-crown-6 at room temperature. 2-methyl-1,4-naphthoquinone was well-miscible with 2-octyl cyanoacrylate. The composition was sterilized by Gamma irradiation at the dose range of 9.8-11.3 kGy. After the sterilization, the composition was evaluated using an advanced aging protocol (American Society for Testing and Materials (ASTM) accelerated aging standard F1980-07), by storing the composition at 80° C. for 13 days. At day 13 of the accelerated aging study, the viscosity and set time of the composition were 20.2 cps and 32.5 seconds, respectively.

Example 4

237.6 g of the activated 2-octyl cyanoacrylate containing 1.354 g of butylated hydroxyanisole, 4.28 mg of $SO_2$, and 1.85 mg of DC violet #2 was mixed with 2.4 g of vitamin K1 oxide, 0.36 g of butylated hydroxyanisole, 24 mg of $SO_2$ solution (7.9%), 12 mg of DC Violet #2, and 48 mg of 18-crown-6 in a three neck round bottom flask equipped with a magnetic stir bar, to which 23 mg of 18-crown-6 was added. Vitamin K1 oxide was miscible with 2-octyl cyanoacrylate composition right away. The composition was sterilized by Gamma irradiation at the dose range of 9.4-11.0 kGy. After sterilization, the increase in viscosity of the composition was 0.71 cps. The average set time of the composition after sterilization was 11.3 seconds.

Example 5

In a three neck round bottom flask equipped with a magnetic stir bar, 0.92 g of 1,4-diacetoxy-2-methylnaphthalene was mixed with 229.08 g of the activated 2-octyl cyanoacrylate that contains 1.649 g of butylated hydroxyanisole, 5.96 mg of $SO_2$, 13.2 mg of DC violet #2, and 46 mg of 18-crown-6 at room temperature. 1,4-diacetoxy-2-methylnaphthalene was well soluble in 2-octyl cyanoacrylate. The composition was sterilized by Gamma irradiation. The average viscosity and set time of the sterile composition were 6.85 cps, and 18.8 seconds, respectively.

Example 6

122.9 g of the activated 2-octyl cyanoacrylate containing 61.5 mg of butylated hydroxyanisole, and 0.37 mg of $SO_2$ was mixed with 1.229 g of 2,3-epoxyphylloquinone, 0.676 g of butylated hydroxyanisole, 7.1 mg of DC Violet #2, and 24.6 mg of 18-crown-6 in a three neck round bottom flask equipped with a magnetic stir bar at room temperature. Vitamin K1 oxide was miscible with 2-octyl cyanoacrylate composition right away. Nevertheless, the composition cured upon Gamma irradiation at the dose range of 9.4-11.0 kGy.

Example 7

In a three neck round bottom flask equipped with a magnetic stir bar, 0.92 g of 2-methyl-3-phytyl-1,4-naphthoquinone was diluted to 230 g by the activated 2-octyl cyanoacrylate that contains 1.306 g of butylated hydroxyanisole, 4.1 mg of $SO_2$, and 1.8 mg of DC violet #2, to which 0.345 g of butylated hydroxyanisole, 23.3 mg of $SO_2$ solution (7.9%), 11.5 mg of DC Violet #2, and 46 mg of 18-crown-6 were added. The mixture was stirred at room temperature and 2-methyl-3-phytyl-1,4-naphthoquinone was well dissolved into 2-octyl cyanoacrylate. The composition was sterilized by Gamma irradiation. The average viscosity and set time of the composition after sterilization was 6.65 cps, and 18.8 seconds, respectively.

Example 8

0.585 g of vitamin K1 oxide was diluted to 116.9 g by the activated 2-octyl cyanoacrylate containing 58.2 mg of butylated hydroxyanisole and 3 ppm of $SO_2$, to which 60.1 mg of $SO_2$ solution (0.579%), 0.292 g of butylated hydroxyanisole, 7.8 ppm DC Violet #2, and 23.4 mg of 18-crown-6 were added. The mixture was stirred at room temperature to give a homogenous solution. The viscosity and set time of the composition were 7.23 cps and 32.5 seconds, respectively. Nevertheless, the composition cured upon Gamma sterilization.

Example 9

In a three neck round bottom flask equipped with a magnetic stir bar, 1.116 g of phylloquinone oxide was mixed with 110.48 g of activated 2-octyl cyanoacrylate containing 0.222 g of butylated hydroxyanisole and 10 ppm of $SO_2$, to which 6.5 mg of DC Violet #2 and 22.3 mg of 18-crown-6 were added. Phylloquinone oxide was well miscible with 2-octyl cyanoacrylate. The composition was sterilized by Gamma irradiation. After the sterilization, the stability of the composition was evaluated via the accelerated aging test at 80° C. for 13 days (American Society for Testing and Materials (ASTM) accelerated aging standard F1980-07). The viscosity of the sterile composition increased from 15.1 cps at day 0 to 4064 cps day 3 of the accelerated aging study at 80° C. The composition cured by day 6 of accelerated aging.

Example 10

12.75 g of vitamin K1 oxide was diluted to 850 by the activated 2-octyl cyanoacrylate containing 4.77 g of butylated hydroxyl anisole and 0.19 g $SO_2$ solution (7.9%) and 7.8 ppm of DC Violet #2, to which 0.133 g of $SO_2$ solution (7.69%), 1.275 g of butylated hydroxyl anisole, 4.3 mg DC Violet #2, and 0.17 g of 18-crown-6 were added. The mixture was stirred at room temperature to give a homogenous solution. The viscosity and set time of the composition were 7.01 cps and 11.3 seconds, respectively. The composition was sterilized by Gamma irradiation.

Example 11

10.85 g of vitamin K1 oxide was diluted to 434 g by the activated 2-octyl cyanoacrylate containing 2.412 g of butylated hydroxyl anisole and 96.4 mg $SO_2$ solution (7.9%) and 7.8 ppm of DC Violet #2, to which 67.7 mg of $SO_2$ solution (7.69%), 0.651 g of butylated hydroxyl anisole, 2.2 mg DC Violet #2, and 86.8 mg of 18-crown-6 were added. The mixture was stirred at room temperature to give a homogenous solution. The viscosity and set time of the composition were 7.09 cps and 12.5 seconds, respectively. The composition was sterilized by Gamma irradiation.

The invention is not limited to the embodiments described and exemplified above, but is capable of variation and modification within the scope of the appended claims.

We claim:

1. A sterilized cyanoacrylate composition, comprising monomeric 2-octyl cyanoacrylate, about 5,000 ppm to about 16,000 ppm of butylated hydroxyl anisole, about 20 ppm to about 150 ppm of sulfur dioxide, about 1% by weight of Vitamin K1 oxide, and optionally about 10 ppm to about 6000 ppm of 18-crown-6 crown ether, wherein the composition is sterilized by irradiation, and the composition does not cure upon irradiation and for at least two years of shelf storage thereafter.

2. The sterilized cyanoacrylate composition of claim 1, wherein the composition comprises about 7,000 ppm to about 16,000 ppm of butylated hydroxyl anisole.

3. The sterilized cyanoacrylate composition of claim 1, wherein the composition further comprises a plasticizing agent.

4. The sterilized cyanoacrylate composition of claim 1, wherein the composition further comprises a thickening agent.

5. The sterilized cyanoacrylate composition of claim 1, wherein the irradiation comprises electron-beam, gamma, x-ray, or microwave irradiation.

6. A kit, comprising the composition of claim 1, a container, and instructions for using the composition in a method for closing a wound on a subject or instructions for using the composition in a method for securing a catheter inserted into the skin of a subject, wherein the container optionally comprises an applicator.

7. The kit of claim 6, wherein the container comprises an ampoule containing the composition.

8. The sterilized cyanoacrylate composition of claim 1, wherein the irradiation comprises gamma irradiation.

9. A sterilized cyanoacrylate composition, comprising monomeric 2-octyl cyanoacrylate, about 5,000 ppm to about 16,000 ppm of butylated hydroxyl anisole, about 20 ppm to about 150 ppm of sulfur dioxide, about 0.5% by weight of Vitamin K1 oxide, and optionally about 10 ppm to about 6000 ppm of 18-crown-6 crown ether, wherein the composition is sterilized by irradiation, and the composition does not cure upon irradiation and for at least two years of shelf storage thereafter.

10. The sterilized cyanoacrylate composition of claim 9, wherein the composition comprises about 7,000 ppm to about 16,000 ppm of butylated hydroxyl anisole.

11. The sterilized cyanoacrylate composition of claim 9, wherein the composition further comprises a plasticizing agent.

12. The sterilized cyanoacrylate composition of claim 9, wherein the composition further comprises a thickening agent.

13. The sterilized cyanoacrylate composition of claim 9, wherein the irradiation comprises electron-beam, gamma, x-ray, or microwave irradiation.

14. The sterilized cyanoacrylate composition of claim 9, wherein the irradiation comprises gamma irradiation.

15. A kit, comprising the composition of claim 9, a container, and instructions for using the composition in a method for closing a wound on a subject or instructions for using the composition in a method for securing a catheter inserted into the skin of a subject, wherein the container optionally comprises an applicator.

16. The kit of claim 15, wherein the container comprises an ampoule containing the composition.

* * * * *